(12) United States Patent
Ou et al.

(10) Patent No.: US 11,589,867 B2
(45) Date of Patent: Feb. 28, 2023

(54) ANISOTROPIC WOUND CLOSURE SYSTEMS

(71) Applicant: Ethicon, Inc., Somerville, NJ (US)

(72) Inventors: Duan Li Ou, Warren, NJ (US); Robert Rousseau, Ottsville, PA (US); Leo B. Kriksunov, Ithaca, NY (US); Julian Quintero, Flemington, NJ (US)

(73) Assignee: Ethicon, Inc., Raritan, NJ (US)

( * ) Notice: Subject to any disclaimer, the term of this patent is extended or adjusted under 35 U.S.C. 154(b) by 289 days.

(21) Appl. No.: 16/885,375

(22) Filed: May 28, 2020

(65) Prior Publication Data

US 2021/0369276 A1 Dec. 2, 2021

(51) Int. Cl.

| | |
|---|---|
| *A61B 17/08* | (2006.01) |
| *A61L 24/00* | (2006.01) |
| *A61L 24/02* | (2006.01) |
| *A61L 24/04* | (2006.01) |
| *A61L 26/00* | (2006.01) |
| *A61B 17/00* | (2006.01) |

(52) U.S. Cl.
CPC .......... *A61B 17/085* (2013.01); *A61L 24/001* (2013.01); *A61L 24/02* (2013.01); *A61L 24/046* (2013.01); *A61L 26/0095* (2013.01); *A61B 2017/00853* (2013.01); *A61B 2017/00884* (2013.01); *A61B 2017/00951* (2013.01); *A61B 2017/086* (2013.01)

(58) Field of Classification Search
CPC .................. A61B 17/08; A61B 17/085; A61B 2017/00853; A61B 2017/00884; A61B 2017/00951; A61B 2017/081; A61B 2017/086; A61L 24/001; A61L 24/02; A61L 24/046; A61L 26/0095
See application file for complete search history.

(56) References Cited

U.S. PATENT DOCUMENTS

| | | | |
|---|---|---|---|
| 2,941,696 | A | 6/1960 | Edwin |
| 3,187,752 | A | 6/1965 | Arthur |
| 3,445,420 | A | 5/1969 | Kookootsedes et al. |
| 3,490,651 | A | 1/1970 | Abplanalp |
| 3,675,821 | A | 7/1972 | Morane et al. |
| 3,775,452 | A | 11/1973 | Karstedt |
| 3,814,730 | A | 6/1974 | Karstedt |
| 4,234,108 | A | 11/1980 | Diamond |

(Continued)

FOREIGN PATENT DOCUMENTS

| | | |
|---|---|---|
| CN | 104531056 A | 4/2015 |
| CN | 105586001 A | 5/2016 |

(Continued)

OTHER PUBLICATIONS

Coogle scholar keyword search (Year: 2021).

(Continued)

*Primary Examiner* — Robert A Lynch

(57) ABSTRACT

Novel compositions and systems for closure of wounds are disclosed. The compositions provide devices of improved flexibility and elasticity and are readily applied to wound sites or over wound closure devices. The present invention is also directed to a novel platinum catalyst for use in such compositions. The catalyst provides for rapid curing on topical surfaces such as skin and bonds to such surfaces in about 2-5 minutes.

20 Claims, 8 Drawing Sheets

(56) References Cited

U.S. PATENT DOCUMENTS

| | | |
|---|---|---|
| 4,340,155 A | 7/1982 | Obrist |
| 4,791,149 A | 12/1988 | Pocknell |
| 5,020,694 A | 6/1991 | Pettengill |
| 5,026,768 A | 6/1991 | Liles |
| 5,211,316 A | 5/1993 | Adalberto et al. |
| 5,431,303 A | 7/1995 | Miskell |
| 5,447,987 A | 9/1995 | Sato et al. |
| 5,577,637 A | 11/1996 | Voss |
| 5,647,510 A | 7/1997 | Keller |
| 5,776,268 A | 7/1998 | Mcjames et al. |
| 5,780,543 A | 7/1998 | Adachi et al. |
| 6,265,480 B1 | 7/2001 | Enami et al. |
| 6,537,246 B1 | 3/2003 | Unger et al. |
| 6,613,185 B1 | 9/2003 | Valade et al. |
| 6,951,654 B2 | 10/2005 | Malcolm et al. |
| 7,393,547 B2 | 7/2008 | Nelson |
| 7,481,333 B2 | 1/2009 | Goldberg et al. |
| 7,798,366 B2 | 9/2010 | Hoshino |
| 3,021,650 A1 | 9/2011 | Tamareselvy et al. |
| 8,357,147 B2 | 1/2013 | Burkinshaw et al. |
| 8,596,499 B2 | 12/2013 | Vogt et al. |
| 8,728,599 B2 | 5/2014 | Fang et al. |
| 8,969,910 B2 | 3/2015 | Katayama |
| 9,038,858 B2 | 5/2015 | Hanai et al. |
| 9,180,476 B2 | 11/2015 | Werner et al. |
| 9,302,282 B2 | 4/2016 | Bertin et al. |
| 9,408,971 B2 | 8/2016 | Carlyon |
| 9,422,404 B2 | 8/2016 | Curtis et al. |
| 9,434,857 B2 | 9/2016 | Ou |
| 9,511,034 B1 | 12/2016 | Garrett |
| 9,642,949 B2 | 5/2017 | Hai et al. |
| 9,649,650 B2 | 5/2017 | Werner et al. |
| 9,655,917 B2 | 5/2017 | Hai et al. |
| 9,764,099 B2 | 9/2017 | Rimsa et al. |
| 10,219,793 B2 | 3/2019 | Quintero et al. |
| 10,441,947 B2 | 10/2019 | Ou |
| 2001/0011162 A1 | 8/2001 | Epstein |
| 2001/0019721 A1 | 9/2001 | Brandt et al. |
| 2002/0076260 A1 | 6/2002 | Heusser |
| 2002/0193879 A1 | 12/2002 | Seder et al. |
| 2003/0044451 A1 | 3/2003 | Mcghee et al. |
| 2003/0077316 A1 | 4/2003 | Nichols et al. |
| 2003/0082223 A1 | 5/2003 | Healy et al. |
| 2003/0183651 A1 | 10/2003 | Greer |
| 2004/0004088 A1 | 1/2004 | Yerby et al. |
| 2004/0181943 A1 | 9/2004 | Kwiecien |
| 2005/0020844 A1 | 1/2005 | Nelson |
| 2005/0029296 A1 | 2/2005 | Hansen et al. |
| 2005/0048124 A1 | 3/2005 | Sarangapani |
| 2005/0127119 A1 | 6/2005 | Keller |
| 2005/0182443 A1 | 8/2005 | Jonn et al. |
| 2005/0256573 A1 | 11/2005 | Seder et al. |
| 2006/0009099 A1* | 1/2006 | Jonn .................... A61L 15/425 442/49 |
| 2006/0134313 A1 | 6/2006 | Guggenbichler et al. |
| 2007/0043332 A1 | 2/2007 | Malcolm et al. |
| 2007/0104665 A1 | 5/2007 | Jones et al. |
| 2007/0293820 A1 | 12/2007 | Dacquay et al. |
| 2008/0054020 A1 | 3/2008 | Pierson et al. |
| 2008/0275403 A1 | 11/2008 | Maaskamp et al. |
| 2009/0004246 A1 | 1/2009 | Woolfson et al. |
| 2009/0026660 A1 | 1/2009 | Nelson et al. |
| 2009/0076480 A1 | 3/2009 | Pudleiner et al. |
| 2009/0108021 A1 | 4/2009 | Hansen et al. |
| 2010/0280547 A1 | 11/2010 | D Alessio et al. |
| 2010/0330025 A1 | 12/2010 | Messersmith et al. |
| 2011/0027753 A1 | 2/2011 | Maurat et al. |
| 2011/0091669 A1 | 4/2011 | Tang et al. |
| 2011/0143148 A1 | 6/2011 | Butts et al. |
| 2011/0272433 A1 | 11/2011 | Vogt et al. |
| 2012/0237461 A1 | 9/2012 | Yu et al. |
| 2012/0328787 A1 | 12/2012 | Marrot et al. |
| 2013/0004586 A1 | 1/2013 | Vachon et al. |
| 2013/0059109 A1 | 3/2013 | Kretschmann et al. |
| 2013/0122314 A1 | 5/2013 | Ou |
| 2013/0123720 A1 | 5/2013 | Lind et al. |
| 2013/0150828 A1 | 6/2013 | Conway |
| 2013/0171265 A1 | 7/2013 | Saxena et al. |
| 2013/0310780 A1 | 11/2013 | Phillips |
| 2013/0310781 A1 | 11/2013 | Phillips et al. |
| 2014/0221522 A1 | 8/2014 | Antoni et al. |
| 2015/0159066 A1 | 6/2015 | Hartwell et al. |
| 2016/0120706 A1 | 5/2016 | Collinson et al. |
| 2016/0220497 A1 | 8/2016 | Caprasse et al. |
| 2016/0354172 A1 | 12/2016 | Krogman et al. |
| 2017/0224823 A1 | 8/2017 | Blanda et al. |
| 2018/0030327 A1 | 2/2018 | Zhang et al. |
| 2018/0163090 A1 | 6/2018 | Ou |
| 2018/0338945 A1 | 11/2018 | Sambasivam |
| 2019/0001019 A1 | 1/2019 | Lindgren et al. |
| 2020/0172740 A1 | 6/2020 | Ou et al. |
| 2021/0369258 A1 | 12/2021 | Ou et al. |
| 2021/0369276 A1 | 12/2021 | Ou et al. |
| 2021/0369639 A1* | 12/2021 | Ou .................... A61K 9/7084 |
| 2021/0371190 A1 | 12/2021 | Ou et al. |
| 2021/0371596 A1* | 12/2021 | Ou .................... B01J 31/127 |
| 2021/0371658 A1* | 12/2021 | Ou .................... C08L 83/04 |
| 2021/0371662 A1* | 12/2021 | Ou .................... C08L 83/04 |

FOREIGN PATENT DOCUMENTS

| | | |
|---|---|---|
| CN | 106009688 A | 10/2016 |
| EP | 3388037 A1 | 10/2018 |
| JP | 11349897 A | 12/1999 |
| KR | 0039498 A | 4/2016 |
| WO | 9725085 A1 | 7/1997 |
| WO | 2010/128855 A2 | 11/2010 |
| WO | 2013/074732 A1 | 5/2013 |
| WO | 2016094084 A1 | 6/2016 |
| WO | 2017158340 A1 | 9/2017 |

OTHER PUBLICATIONS

International Search Report dated Aug. 13, 2021 for International Application No. PCT/IB2021/054533.
International Search Report dated Aug. 18, 2021 for International Application No. PCT/IB2021/054531.
International Search Report dated Feb. 21, 2020 for International Application No. PCT/IB2019/060233.
International Search Report dated Feb. 21, 2020 for International Application No. PCT/IB2019/060235.
International Search Report dated Jan. 11, 2022 for International Application No. PCT/IB2021/054534.
International Search Report dated Jul. 29, 2021 for International Application No. PCT/IB2021/054515.
International Search Report dated Jul. 30, 2021 for International Application No. PCT/IB2021/054518.
IP.com search of the PGPub (Year: 2021).
Lewis, et al., The chemistry of fumarate and maleate inhibitors with platinum hydrosilylation catalysts, Journal of Organometallic Chemistry, 1996, pp. 221-227, vol. 521 Issue 1.

* cited by examiner

FIG. 1a
FIG. 1b
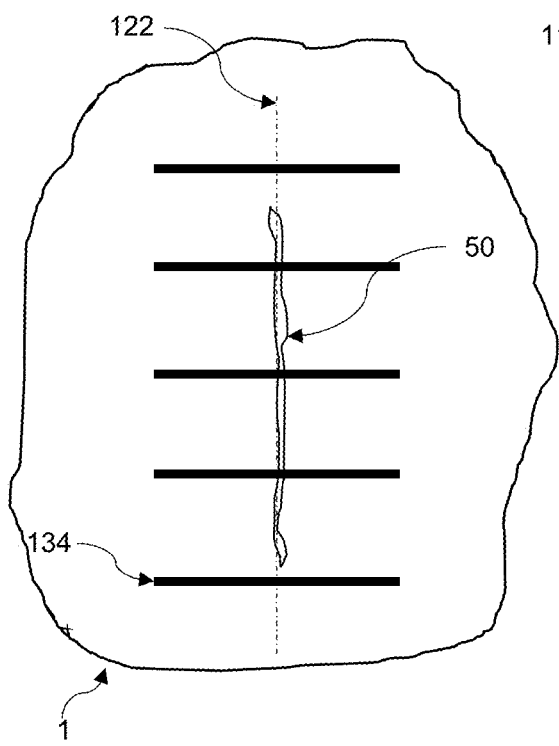
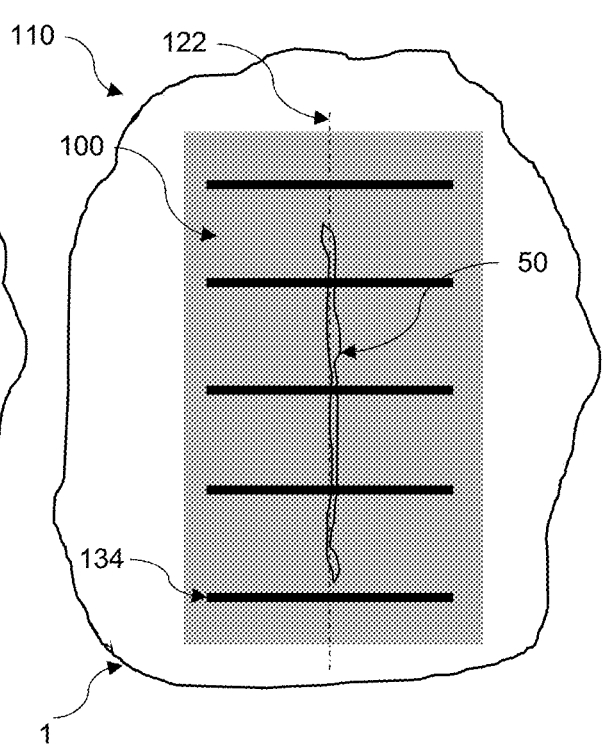

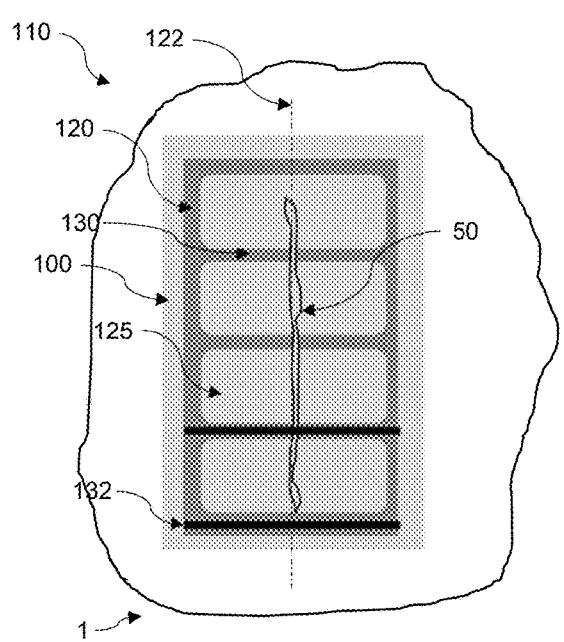 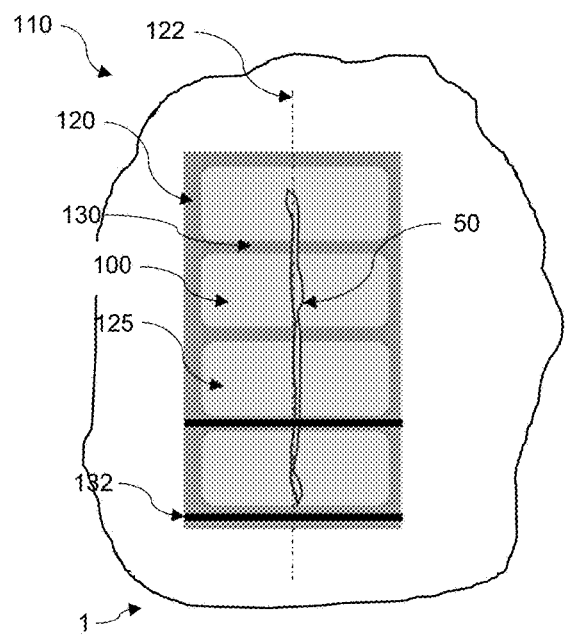
FIG. 2a  FIG. 2b

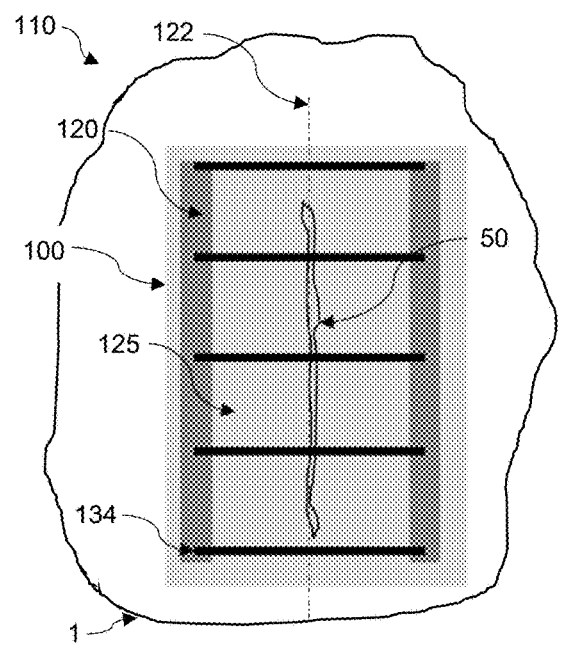 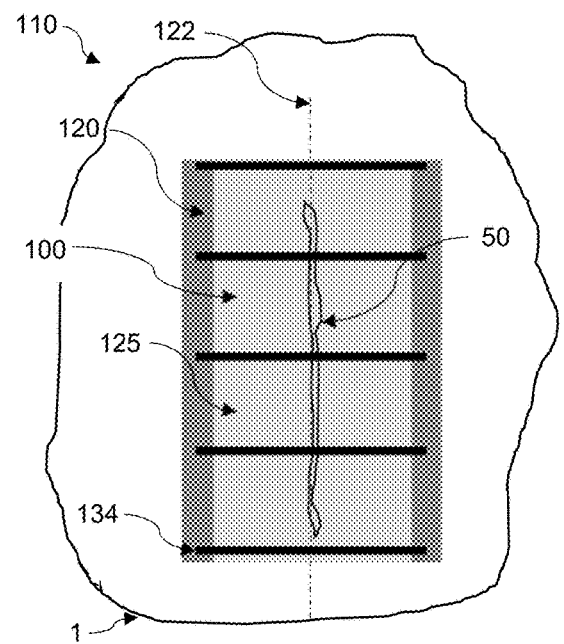
FIG. 3a      FIG. 3b

ANISOTROPIC WOUND CLOSURE SYSTEMS

CROSS-REFERENCE TO RELATED APPLICATION(S)

This application is related to U.S. Non-Provisional Application Ser. Nos. 16/885,413, 16/885,426, 16/885,361, and 16/885,366, being filed concurrently herewith and having a common assignee the contents of which are herein incorporated by reference in their entirety for all purposes.

TECHNICAL FIELD

The field of art to which this invention pertains is silicone-based wound closure compositions devices and systems, in particular, silicone-based topical skin adhesives (TSA's) and wound closure systems which incorporate such adhesives.

BACKGROUND OF THE INVENTION

There is a need for elastomeric topical skin adhesives, especially for skin closure of the moving body joints such as knees, wrists, elbow, etc.

Elastic versions of the TSA are especially needed in orthopedic surgery. Aggressive motion of joints may compromise the quality of the closure at the interface between the adhesive and the skin. Watertight closure is also desirable in a product in order to lessen the possibility of post-surgical infections. Silicone types of adhesives are one solution for both these two key customer requirements due to its elasticity and sealing properties.

Silicone is known for its inertness and commonly used as OTC scar reduction products. Reducing skin reactions and improvement of cosmesis are the extra benefits provided by silicone-based TSA.

Thus, there is a need for elastomeric topical skin adhesives, especially for the closure of the moving body parts and joints, such as knees, wrists, elbows, etc.

SUMMARY OF THE INVENTION

Accordingly, novel catalytic compositions, silicone based curable adhesive compositions, and wound closure systems are disclosed.

The compositions comprise a mixture of vinyl terminated polydimethylsiloxane, and polydimethylhydro-co-polydimethylsiloxane cross linker, surface treated silica particles as bonding agent, and a novel, non-conventional platinum catalyst, optionally with common low boiling point organic solvent such as aliphatic organic solvent such as hexane or its commercial derivatives, and SiH terminated polydimethyl siloxane chain extender. The proposed silicone adhesive can be dried on skin at body temperature in less than 3 minutes. The skin holding forces between the proposed silicone adhesive and skin is comparable or better than the typical cyanoacrylate-based TSA products. Unlike the traditional cyanoacrylate-based TSA products, the invented silicone-based TSA when combined with traditional wound closure devices can be stretched to 160% of its original length and fully recover to its original dimension.

The bonding formation is enabled by the condensation reaction between the silanol functions on the surface of silica particle and the OH functions on the skin. Silanol condensation tends to be sluggish at ambient temperature and the novel non-conventional catalyst enables this reaction to occur in a short period of time. The platinum based novel catalyst also activates vinyl silylation reaction to allow vinyl terminated silicone polymer to cross link simultaneously to the condensation reaction.

In general, the present invention relates to a wound closure system comprising:
 a) an anisotropic wound closure device; and
 b) a coating composition comprising:
  a cross-linkable silicone polymer having reactive functionalities;
  a silica-containing composition;
  a silicone cross-linking agent; and,
  a catalyst, wherein said catalyst comprises a platinum tetramethyldivinyl disiloxane diethyl maleate complex having the formula:

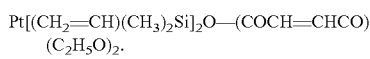

In the foregoing embodiment, the silica-containing composition may be added as a separate component, but more preferably it is contained in the cross-linkable silicone polymer.

In one embodiment, the system comprises a wound closure device comprising one or more tie-bars.

In another embodiment, the system comprises a wound closure device comprising a longitudinal wound closure strip with one or more tie bars incorporated across the longitudinal axis of the strip.

In yet another embodiment, the system comprises a wound closure device comprising a longitudinal wound closure strip with one or more tie bars incorporated across the longitudinal axis of the strip further comprising windows

BRIEF DESCRIPTION OF THE DRAWINGS

FIGS. 1a and 1b depict an embodiment using tie bars and a silicone film of this invention.

FIGS. 2a and 2b show another embodiment comprising a longitudinal wound closure strip with one or more tie bars incorporated across the longitudinal axis of the strip and a silicone film of this invention.

FIGS. 3a and 3b depict yet another embodiment comprising a longitudinal wound closure strip with one or more tie bars incorporated across the longitudinal axis of the strip further comprising windows and a silicone film of this invention

DETAILED DESCRIPTION OF THE INVENTION

Figure 4A:
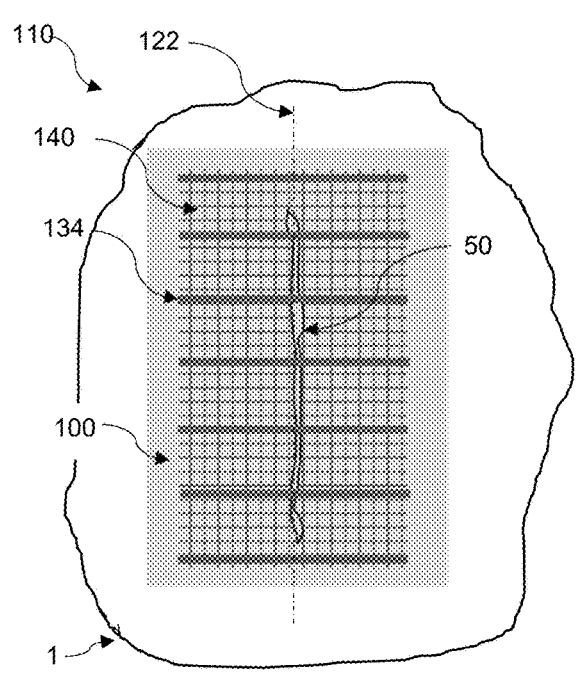
FIGS. 4a and 4b show another embodiment comprising a longitudinal wound closure strip with one or more tie bars incorporated across the longitudinal axis of the strip and a silicone film of this invention.

The terms silicone and siloxane are conventionally used interchangeably in this art, and that usage has been adopted herein.

Topical Skin Adhesive Compositions & Wound Closure Systems

One aspect of the present invention is directed to novel wound closure compositions which are particularly useful for closing lacerations and surgical incisions. These compositions are suitable for use as topical skin adhesives and as adhesives in conjunction with wound closure devices.

In one embodiment, the compositions include a mixture of a cross-linkable siloxane polymer and a silica-containing composition which may be added as a separate component, but more preferably contained in the cross-linkable silicone polymer, a conventional silicone cross-linking agent, and a platinum catalyst. The silicone polymer components are blended with conventional aromatic organic solvents, including, for example, aliphatic organic solvents (such as, for example, hexane, heptane or its commercial derivatives) to form coating solutions or compositions. Other solvent suitable for coating solution includes and not limited to low molecular weight siloxane, e.g., hexamethyldisiloxane.

The cross-linkable siloxane polymers useful in the compositions of the present invention will have reactive functionalities or terminal functional groups, including but not limited to vinyl terminated, hydroxyl and acrylate functional groups. The cross-linkable siloxane polymers that can be used in the compositions of the present invention preferably include vinyl terminated polydialkylsiloxane or vinyl terminated polyalkyarylsiloxane. Examples include but are not limited to the following vinyl terminated siloxane polymers: polydimethyl siloxane, polydiphenylsilane-dimethylsiloxane copolymer, polyphenylmethylsiloxane, polyfluoropropylmethyl-dimethylsiloxane copolymer and polydiethylsiloxane. It is particularly preferred to use vinyl terminated cross-linkable polymethyl siloxane.

The cross-linking agents that can be used in the compositions of the present invention include conventional silicone cross-linking agents such as, for example, polymethylhydrosiloxane, polymethylhydro-co-polydimethylsiloxane, polyethylhydrosiloxane, polymethylhydrosiloxane-co-octylmethylsiloxane, polymethylhydrosiloxane-co-methylphenylsiloxane. The preferred conventional crosslinkers for use in the compositions of the present invention are polymethylhydro siloxane and polymethylhydro-co-polydimethylsiloxane. Precise control of cross-link density in the coatings of the present invention is achieved by precise control of the ratio of non-cross-linkable silicone polymer (e.g., polydimethylsiloxane) to fully cross-linked polymer. The fully cross-linked polymer is formed by a reaction between the functionalized cross-linkable polymer and the cross-linking agent, for example, a vinylsilylation reaction between vinyl-terminated polydimethylsiloxane and polymethylhydrosiloxane optionally in the presence of a platinum complex catalyst. Examples of this polymer include but are not limited to: Gelest Product Code No. DMS-V31, DMS-V33, DMS V-35, DMS V42, DMS-V46, DMS-V52, etc., available from Gelest, Inc., Morrisville, Pa. 19067. The typical molecular structure of vinyl terminated polydimethyldisiloxane is the following:

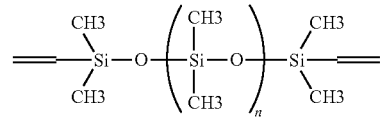

wherein n is defined by the molecular weight.

The molecular weights of the silicone polymers used wherein can be estimated based on the relationship between viscosity and molecular weight (page 11, SILICONE FLUIDS: STABLE, INERT MEDIA ENGINEERING AND DESIGN PROPERTIES, Catalog published by Gelest, Inc. 11 East Steel Rd. Morrisville, Pa. 19067). Using A. J. Barry's relationship for molecular weights (M)>2,500 correlating the kinematic viscosity p expressed in centistokes (cSt) at 25 C, the molecular weight M of silicones can be estimated as follows:

$$\log \mu_{eSi} = 1.00 + 0.0123\ M^{0.5}$$

(as published by A. J. Barry in the *Journal of Applied Physics* 17, 1020 (1946))

Vinyl terminated polydimethylsiloxane reacts with polymethylhydrosiloxane cross-linker in the presence of platinum catalyst under appropriate conditions; the vinyl terminated polydimethylsiloxane linear polymers are fully cross-linked to each other as the result of this reaction. The amount of polymethylhydrosiloxane cross-linker is in large stoichiometric excess compared to vinyl terminated polydimethylsiloxane base polymer. It is believed that the extra SiH functions in the cross-linker react with the OH functions on the surface such as human skin, e.g., polymeric sutures, to form Si—C—C bonds at elevated temperature or in the case of steel needles, to form Si—O—Fe bonds. Covalent bonds thus created between the silicone coating and the device, as the result of this reaction, result in the adhesive attachment of the coating to a given surface.

The polymethyhydrosiloxane cross-linkers, or cross-linking agents, used in the practice of the present invention will have a molecular weight between about 1000 and about 3000, and preferably between about 1400 and about 2100. An example of this polymer cross-linker includes, but is not limited to, Gelest Product Code No. HMS-991, HMS-992, available from Gelest, Inc., Morrisville, Pa. 19607. The typical molecular structure of the polymethylhydrosiloxane cross-linker is the following:

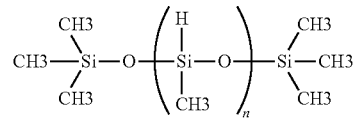

wherein n is defined by the molecular weight.

Polymethylhydro-co-polydimethylsiloxane can also be used as cross-linker or cross-linking agent in the novel coatings of the present invention. Examples of this polymer include, but are not limited to, Gelest Product Code No. HMS-301, HMS-501. The molecular weight of this siloxane polymer cross-linking agent will typically be between about 900 and about 5,000, and preferably about 1,200 to about 3,000. The typical molecular structure of polymethylhydro-co-polydimethylsiloxane cross linker is the following:

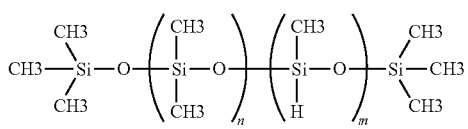

wherein n and m are defined by the molecular weight.

Silica-Containing Compositions

As used herein, the silica-containing compositions described for use with this invention include silica materials as a separate component (such as surface treated silica) or from commercially available compositions that contain silica in a cross linkable silicone polymer mixture.

As a separate component, silica is incorporated into composition of this invention to act as a bonding agent to skin and other substrate materials. It is believed that the OH groups on the surface of silica particles react with the OH functions on the surface of substrate material including human skin under a certain condition, as illustrated below.

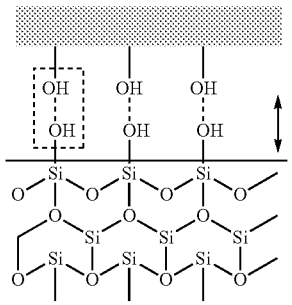

Silica particles were incorporated into the cross linkable silicone polymers. Hexamethyl silyl surface treatment is needed for the silica particles to enable its compatibility to the polysiloxane polymer matrix and to prevent phase separation. An example of treated silica includes hexamethyldisilazane treated silica i.e., trimethyl silyl surface treated silica filler (Gelest SIS6962.0).

In the case of silicone polymers already containing silica, these may be obtained from commercially available sources such as silica-containing composition selected from reactive silica-containing silicone bases including HCR (high consistent rubber) bases and LSR (liquid silicone rubber) bases, preferred are LSR bases. Other commercial examples of this material include and is not limited to Wacker 401-10, 401-20, 401-40 base; and a liquid silicone rubber base, a commercial example of this material includes and is not limited to Bluestar Silbione LSR 4370 base. These type of commercial silicone rubber bases are prepared by mixing a surface-treated silica filler with various molecular weights of vinyl terminated polydimethylsiloxane polymer. In-situ surface treatment may be performed during the mixing process to improve the compatibility between filler and polysiloxane polymer.

Catalyst

Karstedt of GE Silicone invented a highly active platinum catalyst at the beginning of the 1970's (U.S. Pat. No. 3,775,452). Vinyl terminated polydimethylsiloxane can react with polymethylhydrosiloxane containing cross linker in less than 1 minute at ambient temperature with as little as 10 ppm of the Karstedt catalyst. The traditional platinum catalyst does not enable the reaction between OH groups on the surface of silica particles and the OH functions on the surface of substrate. This type of condensation reaction tends to be slow at ambient condition and the typical catalyst for this reaction including organic amine and catalyst such as tin dilaurate. Trace amounts of condensation catalyst will terminate the catalytic ability of platinum catalyst and this phenomenon is referred to as platinum poisoning in the silicone industry. A novel platinum comparable catalyst is needed to activate the OH condensation between silica particles and substrate materials and to enable rapid adhesion formation between silicone and a given substrate material. A platinum based novel catalyst of the present invention is able to activate both vinyl silylation and OH condensation simultaneously.

The novel catalyst is prepared by reacting Karstedt's catalyst with diethyl maleate according to scheme 1. The novel platinum tetramethyldivinyl disiloxane diethyl maleate catalyst enables both vinyl silylation and condensation reaction. This is referred to as "dual functional silicone catalyst".

Scheme 1

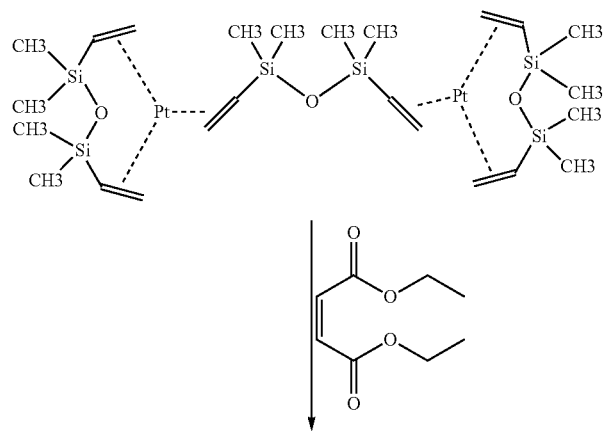

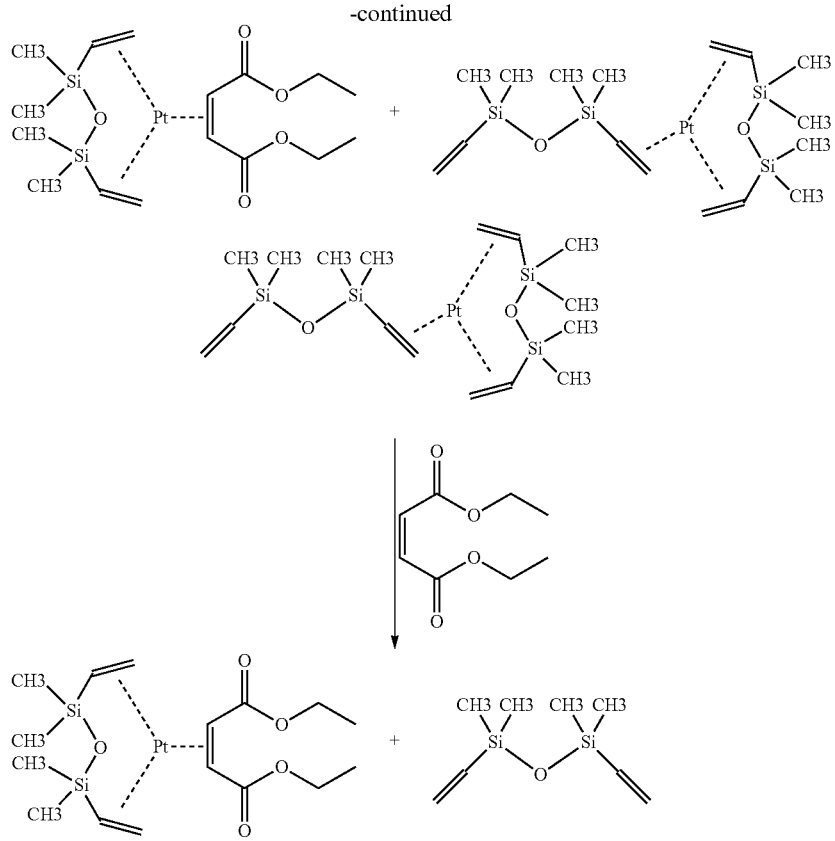

The novel catalyst of the present invention may be prepared in the following manner. Karstedt catalyst in xylene solution is mixed with a low concentration of vinylcyclohexanol in a xylene solution at ambient temperature for a sufficiently effective time to complete the reaction, e.g., a half an hour, and completion of the reaction is indicated by a change of the color of the reaction mixture, from clear to light brown.

The resulting catalyst solution containing the novel catalyst of the present invention is ready to use in a composition useful as a topical skin adhesive. The formula of the resulting platinum complex catalyst (platinum tetramethyldivinyl disiloxane diethyl maleate complex) is:

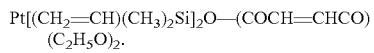

It should be noted that the resulting catalyst reaction mixture will contain a small amount of the reaction product divinyltetramethyldisiloxane. This component does not affect the catalyst and is a low boiling point component that is rapidly evaporated. Accordingly, purification of the catalyst mixture to remove divinyltetramethyldisiloxane is optional, and it is believed that its presence at ultra low concentrations will not affect the cross-linking reaction of a cross-linkable silicone polymer. The novel catalyst of the present invention also actives the bonding formation between silanol groups on the surface of silica fillers and OH functions on a given surface, that is, the catalyst is capable to activate two reactions. This allows for curing the cross-linkable components in silicone coatings to rapidly form coating films at desired curing temperatures and provides bonding to a given substrate such as human skin.

Solvents for Viscosity Reduction

Some commercially produced filler reinforced cross linkable silicone polymers (silicone base rubber) have high viscosity, typically higher than 500,000 and up to many millions of cP. It is impossible to mix and spread such high viscosity material onto skin and low hazardous organic solvent is needed to reduce its viscosity.

Low temperature aliphatic solvents are used for this purpose. Typical examples include, but are not limited to, pentanes, heptanes, hexanes and their mixtures. The organic solvents are added at a concentration sufficient to allow effective blending of the silicone polymer components into a homogeneous solution. The total solvent concentration is between 10% and 30%, depending upon the original viscosity of the base rubber. Ultra-low boiling point solvent such as n-butane and isopentane can also been used to provide sprayable formulation of silicone adhesive.

Chain Extender for Low Viscosity Vinyl Terminated Polydimethylsiloxane Base Polymer For those commercially produced filler reinforced cross linkable silicone polymers (silicone base rubber) that have a high viscosity in the range from 100,000 centipoise (cP) to several million cP (e.g., 1-20 million cP) viscosity, (low molecular weight) vinyl terminated polydimethylsiloxane (<300 cP) may be also added together with low temperature aliphatic solvents to improve its mixability and spreadability. A SiH terminated polydimethylsiloxane is added as a chain extender to polymerize the low molecular weight vinyl terminated polydimethylsiloxane. The SiH terminated polydimethylsiloxane base polymer has molecular weight between 1000 and 100,000, preferably between 3,000 to 10,000.

Examples of this type of polymer include, but are not limited to: Gelest Product Code No. DMS-H21, DMS-H31, etc. The typical molecular structure of SiH terminated polydimethyldisiloxane is illustrated below

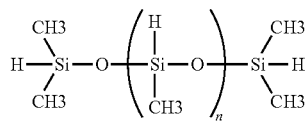

The above silicone polymers and novel platinum catalyst are dispersed into low boiling point organic solvents to form the coating solution. Low temperature aliphatic solvents are used for the silicone dispersion. Aromatic solvents and hexamethyldisiloxane are commonly used for silicone dispersion. Typical examples include, but are not limited to, pentane, heptanes, hexane and their mixtures. The organic solvents are added at a concentration sufficient to allow effective blending of the silicone polymer components into a homogeneous coating solution. The total solvent concentration is from about 80 wt. % to about 99 wt. %, and is more typically from about 85 wt. % to about 93 wt. %, depending upon the coating thickness requirement. Those skilled in the art will appreciate that the coating thickness can be engineered by changing the solids content of the coating solution.

The sequence of the addition of components is important. The typical coating composition is prepared in the following manner. In the case when the silica is added as a separate component, the vinyl terminated polydimethylsiloxane is dispersed into the first solution such as hexamethyldisiloxane together with surface treated silica for up to two hours until fully homogeneous (solution 2). Heptane is then added (solution 3) and further mixing for one hour prior to the addition of polymethylhydrosiloxane cross linker. The solution is fully blended for one more hour after all of the catalyst is added as the final component In the following paragraph, the wt. % is the wt. % of total solid content in the coating solution. The novel coating compositions of the present invention will contain sufficient amounts of the polymeric components, silica-containing composition, cross-linking agent, catalyst, and solvent to effectively provide a silicone coating having high flexibility and durability.

Typically, the amount of the silica in the coating solution will be about 5 wt. % to about 40 wt. % (total solids), more typically about 10 wt. % to about 30 wt. % (total solids), and preferably about 15 wt. % to about 25 wt. % (total solids). The amount of the cross-linkable silicone polymer will typically be about 60 wt. % to about 95 wt. % (total solids), more typically about 70 wt. % to about 90 wt. % (total solids), and preferably about 75 wt. % to about 85 wt. % (total solids). The amount of the silicone cross-linking agent will typically be about 1 wt. % to about 15 wt. % (total solids), more typically about 2 wt. % to about 10 wt. % (total solids), and preferably about 3 wt. % to about 8 wt. % (total solids). The amount of the platinum catalyst based upon the total solids in the novel silicone coating compositions (platinum element in total solids) of the present invention will typically be about 0.06 wt. % to about 0.003 wt. %, more typically about 0.04 wt. % to about 0.008 wt. %, and preferably about 0.03 wt. % to about 0.01 wt. %.

The amount of organic solvent in the compositions of the present invention will typically be about 0 wt. % to about 30 wt. %, more typically about 10 wt. % to about 20 wt. %, and preferably about 12 wt. % to about 18 wt. %. Those skilled in the art will appreciate that the amount of solvent present in the novel coating compositions of the present invention will vary with several factors, and that the solvent quantity in the coating compositions will be selected to engineer an efficacious coating. The factors typically considered include the method of application, the method of cure, the coating equipment utilized, ambient conditions, thickness, etc. It will be appreciated that each of the components of the coating compositions of the present invention may consist of blends of those components. For example, two or more cross-linkable silicone polymers having different functionalities and/or molecular weights may be used, etc.

The compositions of this invention are well suited for wound closure applications such as topical skin adhesives. Generally, these compositions have been demonstrated to cure at temperatures at about 19 C. At temperatures of about 28 C, the compositions cure in about 2-5 minutes.

As noted above and as would be appreciated by one of skill in the art, the silicone compositions of this invention cure in several minutes to films that are neither sticky nor tacky. In contrast, some silicone adhesives, such as silicone pressure sensitive adhesives (PSA's), are by nature sticky or tacky and are intended to be such for the entire usable life of the adhesive. Such useable life of the tacky silicone PSA's may be upwards to several years. The non-tackiness of the compositions and examples of this invention is measured by ASTM C679.

In general ASTM C679 consists of lightly touching a surface of a curing sealant with a polyethylene film at regular intervals until the sealant does not attach itself to the film and the film appears clean when peel from the surface. More specifically a strip of polyethylene film is placed on the surface of the curing elastomer and a 30 g weight is placed on the film. The weight is left in place for 30 seconds, then removed and the polyethylene strip is removed and examined for sealant attachment to the film. The length of time from when the sealant was first applied onto a given surface until the time the sealant is no longer picked up by the film is called tack-free time and is the time point at which the film exhibits a non-tacky nature which evidences that the sealant has cured.

Upon curing the curable compositions of the present invention exhibit stretchable, flexible and elastic properties especially useful for applications over wound closure sites on bendable joints, such as knees, elbows. The curable compositions of the present invention, optionally in combinations with various wound closure devices can be applied over any wound closure site, including over bendable joints as well as relatively low mobility wound closure sites, such as general surgical closures such over any tissue area, e.g. body, abdominal, arm, leg, shoulder, back areas and similar.

The compositions of this invention can be applied onto wounds directly as a curable liquid or semi-liquid, flowable composition, or applied over a porous, flowable composition-permeable wound closure device.

Anisotropic Wound Closure Systems

As noted above, the compositions of this invention are suitable for use in combination with wound closure devices. The wound closure devices of this invention are anisotropic in nature, i.e., they stretch or bend more in one direction than another and come in various embodiments as hereinafter described. In this invention, the devices stretch along their longitudinal axis while resisting stretching across their lateral axis.

Tie Bar Embodiments

According to one embodiment of the present invention and referring to FIGS. 1a and 1b, wound closure system 110 comprises a plurality of reinforcing tie-bars 134 arranged perpendicularly along axis 122 of wound 50 on a substrate such as skin 1. In FIG. 1b, silicone adhesive of this invention is applied over the pre-fixed tie bars 134 by spreading or spraying methods to form a flexible film 100 and complete wound closure system 110.

Wound closure system 110 is configured to be stretchable and elastic, with non-destructive elongation along axis 122 of at least 100%. Wound closure system 110 configured with tie bars 134 is reversibly stretchable along axis 122 at least 150% under a force of 10 N for a strip of film 100 that is 2.5 cm wide and 15 cm long.

Tie-bars 134 represent flat ribbons, or elongated shape of any cross-section, such as elliptical, round, square, triangular, or similar cross-section. Still yet, tie-bars 134 can be formed in-situ from cyanoacrylate stripes (or other cross linkable non-elastic adhesive), applied as a line across the wound or delivered via a template to provide inelastic bridge structures Tie-bars 134 can be positioned on the wound and attached adhesively. Tie-bars 134 are resistant to stretching in the direction perpendicular to axis 122 due to its dimension, i.e. in the direction aligned with tie-bars. Tie-bars 134 preferably are made of material that is non elastic or resists stretching when part of wound closure system 110. Tie-bars 134 typically will have a width between 0.5 to 2 mm and 2.5 to 5 cm length and thickness between 0.5 to 3 mil (approximately 0.01-0.08 mm).

Due to presence of silicone as matrix material 100, the wound closure systems 110 of this invention has similar stretchability along axis 122 as silicone film, but restricted stretchability in the direction perpendicular to axis 122 due to the presence of the tie bars 134.

In some embodiments, the silicone tie bar composite (wound closure system 110) has stretchability in the direction perpendicular to axis 122 that is 20%, 10%, 5%, or less, of stretchability in the direction along axis 122; preferably there is no stretchability or limited stretchability in the direction perpendicular to axis 122.

Tie bars may optionally have a pressure sensitive adhesive on one side thereof.

In operation, tie bars 134 are positioned on tissue 1 over a wound 50 over a bendable joint with axis 122 aligned with the wound and the limb, the wound is approximated using the tie bars 134. A rapidly polymerizable or cross-linkable silicone adhesive having elastic and stretchable properties when cured, is then applied onto the area as illustrated in FIG. 1b as 100. The adhesive is allowed to fully cure to a non-tacky or non-sticky film 100. Advantageously, tie bars 134, now fully adherent to tissue and protecting the wound, allows bendability of the joint by stretching in the direction along axis 122, but is resisting wound dehiscence by resisting stretching across axis 122 (i.e. perpendicular to axis 122).

Window Embodiments

According to another embodiment of the present invention as illustrated in FIGS. 2a and 2b, elastic wound closure system 110 comprises a flexible, flat, areal, non-porous, elongated window substrate 120 having longitudinal axis 122 and a plurality windows or cut-outs 125 arranged perpendicularly to axis 122 of wound 50 on tissue substrate 1. Adhesive shown as cured film 100 may completely cover window substrate 120 and go beyond the margins of window substrate 120 (FIG. 2a) or may conterminously cover window substrate 120 (i.e., within the margins of window substrate 120 (FIG. 2b)).

Areas of window substrate 120 between windows 125 form reinforcing tie-bars 130. Window substrate 120 can be further reinforced with a plurality of tie bars 132. While FIGS. 2a and 2b depict 2 ties bars 132, additional, fewer or no tie bars 132 may be employed. Window substrate 120 can be rectangular, as shown, or ellipsoidal, or of any geometric shape that is flat and elongated.

Window substrate 120 is configured to be stretchable and elastic, with non-destructive elongation along axis 122 of at least 20%. Window substrate 120 is configured to reversibly stretch along axis 122 at least 20% under force of 10 N for a strip that is 2 cm wide and 15 cm long.

Window substrate 120 can be made of the same silicone material as the silicone adhesive, or any other fully compatible material.

Tie-bars 130 can be formed directly from the same material as window substrate 120 and be formed during formation of window substrate 120. Alternatively, tie-bars 132 can be positioned on the window substrate 120 and attached adhesively, laminated, welded, or similar. Tie-bars 130, 132 represent round filaments or flat ribbons, or elongated shape of any cross-section, such as elliptical, round, square, triangular, or similar cross-section.

Alternatively, tie-bars 132 can be 3D printed on window substrate 120. Alternatively, tie-bars 132 can be incorporated or embedded into window substrate 120. Still yet, tie-bars 132 can be formed in-situ from cyanoacrylate stripes (or other cross linkable non-elastic adhesive), applied as a line across the wound or delivered via a template to provide inelastic bridge structures.

In another embodiment, as depicted in FIGS. 3a and 3b, tie-bars 134 form windows 125 as shown, with tie-bars 134 representing round, or flat filaments or ribbons positioned across axis 122. Adhesive shown as cured film 100 may completely cover window substrate 120 and go beyond the margins of window substrate 120 (FIG. 3a) or may conterminously cover window substrate 120 (i.e., within the margins of window substrate 120 (FIG. 3b))

Tie-bars 130, 132, 134 are resilient against stretching in the direction perpendicular to axis 122, i.e. in the direction aligned with tie-bars 130, 132, 134. Tie-bars 130, 132, 134 are made of the material that is much less elastic and much less stretchable than the material of window substrate 120, or are made of the same material, but are having higher thickness than film forming window substrate 120, such as having thickness that is 2, 3, 5, or 10 times the thickness of film forming window substrate 120.

Due to presence of tie-bars 130, 132, 134 wound closure system 110 has substantially similar stretchability along axis 122 as window substrate 120, but much lesser stretchability than window substrate 120 in the direction perpendicular to axis 122. In some embodiments, wound closure system 110 with tie-bars 130 or 132, 134 has stretchability in the direction perpendicular to axis 122 that is 20%, 15%, 10%, 5%, or less, of stretchability in the direction longitudinal to axis 122 of the window substrate 120 itself.

In one embodiment, window scaffold 120 with tie-bars 130 or 132, 134 has stretchability that is less than 20% than stretchability of window substrate 120 itself (without any reinforcing tie-bars 130, 132, 134), in the direction perpendicular to axis 122.

In one embodiment, under force of 10 N applied perpendicular to axis 122, window substrate 120 elongates at least 2 mm, while window scaffold 110 with tie-bars 130, 132, 134 elongates less than 0.5 mm, for a strip that is 2 cm wide and 3 cm long.

Window scaffold 120 can have optional pressure sensitive adhesive on one side thereof.

In operation, window scaffold 120 is positioned on tissue over a wound 50 over a bendable joint with axis 122 aligned with the wound 50 and the limb. The wound is approximated using window scaffold 120. A rapidly polymerizable or cross-linkable adhesive having elastic and stretchable properties when cured, is then applied over window scaffold 120. The adhesive is allowed to fully cure to form non-tacky or non-sticky film 100. Advantageously, wound closure system 110, now fully adherent to tissue 1 and protecting wound 50 allows bendability of the joint by stretching in the direction along axis 122, but resists wound 50 dehiscence by resisting stretching across axis 122 (i.e. perpendicular to axis 122).

Mesh Embodiments

Figure 4B:
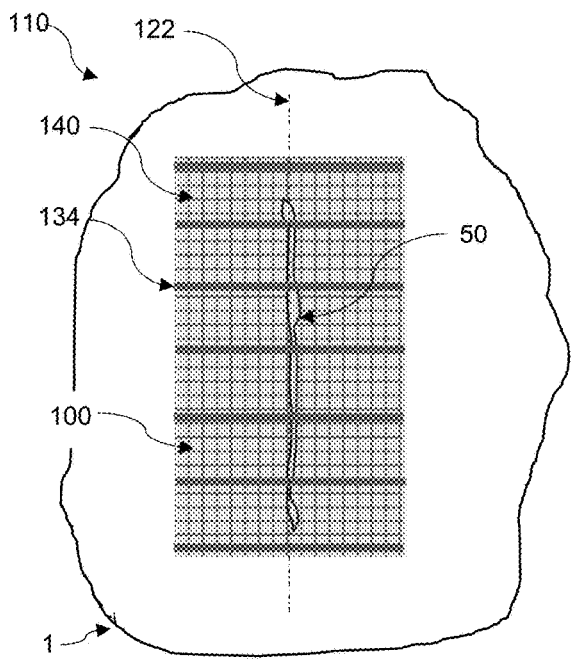

According to yet another embodiment of the present invention, as depicted in FIGS. 4a and 4b, wound closure system 110 comprises a flexible, flat, areal, porous, elongated mesh substrate 140 having longitudinal axis 122 and a plurality of reinforcing tie-bars 134 arranged perpendicularly to the axis 122. Mesh substrate 140 can be rectangular, as shown, or ellipsoidal, or of any geometric shape that is flat and elongated. Adhesive shown as cured film 100 may completely cover window substrate 120 and go beyond the margins of window substrate 120 (FIG. 4a) or may conterminously cover window substrate 120 (i.e., within the margins of window substrate 120 (FIG. 4b)).

Elongated mesh substrate 140 is configured to be stretchable and elastic, with plastic, non-destructive elongation along axis 122 of at least 20%. Elongated mesh substrate 140 is configured to reversibly stretch along axis 122 at least 20% under force of 10 N for a strip that is 2 cm wide and 15 cm long.

Tie-bars 134 represent round filaments or flat ribbons, or elongated shape of any cross-section, such as elliptical, round, square, triangular, or similar cross-section. Still yet, tie-bars 134 can be formed in-situ from cyanoacrylate stripes (or other cross linkable non-elastic adhesive), applied as a line across the wound or delivered via a template to provide inelastic bridge structures Tie-bars 134 can be positioned on the mesh substrate 140 and attached adhesively, laminated, welded, or similar. Alternatively, tie-bars 134 can be 3D printed on mesh substrate 140. Alternatively, tie-bars 134 can be incorporated or embedded into mesh substrate 140 Alternatively, tie-bars 134 can be formed directly from the same material as mesh substrate 140 and be formed during forming of mesh substrate 140 such as by weaving.

Tie-bars 134 are resilient against stretching in the direction perpendicular to axis 122, i.e. in the direction aligned with tie-bars 134. Tie-bars 134 are made of the material that is much less elastic and much less stretchable than material of mesh substrate 140, or are made of the same material, but may have a larger cross-section than fibers or filaments forming mesh substrate 140, such as having diameter that is 2, 3, 5, or 10 times the diameter of fibers or filaments forming mesh substrate 140. In case of tie-bars 134 having a ribbon shape, they can be made of the same material as mesh substrate 140, but with higher thickness, such as 2, 3, 5, 10 times thicker.

Due to presence of tie-bars 134, wound closure system 110 has substantially similar stretchability along axis 122 as mesh substrate 140, but much lesser stretchability than mesh substrate 140 in the direction perpendicular to axis 122. In some embodiments, wound closure system 110 with tie-bars 134 has stretchability in the direction perpendicular to axis 122 that is 5%, or less, of stretchability in the direction longitudinal to axis 122 of the mesh substrate 140 itself.

In one embodiment, wound closure system 110 with tie-bars 134 has stretchability that is less than 20% than stretchability of the mesh substrate 20 itself (without any tie-bars 134), in the direction perpendicular to axis 122.

In one embodiment, under force of 10 N applied perpendicular to axis 122, mesh substrate 140 elongates at least 2 mm, while wound closure system 110 with tie-bars 134 elongates less than 0.5 mm, for a strip that is 2 cm wide and 3 cm long.

Mesh substrate 140 can have optional pressure sensitive adhesive on one side thereof.

In operation, mesh scaffold 140 is positioned on tissue over a wound 50 over a bendable joint with axis 122 aligned with the wound and the limb, the wound is approximated using mesh scaffold 140. A rapidly polymerizable or cross-linkable adhesive having elastic and stretchable properties when cured, is then applied over mesh scaffold 140. The adhesive is allowed to fully cure to non-tacky or non-sticky film 100. Advantageously, wound closure system 110, now fully adherent to tissue and protecting the wound, allows bendability of the joint by stretching in the direction along axis 122, but is resisting wound 50 dehiscence by resisting stretching across axis 122 (i.e. perpendicular to axis 22).

Wound closure devices suitable for use in this invention comprise any device that is configured to close a wound. The wound closure devices most useful are wound closure strips, tapes, patches or any other materials suitable for closing a wound, most preferably a strip. Preferably, the wound closure device is porous and will allow a flowable, polymerizable adhesive to permeate the device and to allow adequate bonding of the device to a tissue surface being bonded.

The wound closure device comprises a wound facing side and a top side. The wound facing side may further comprise an adhesive such as a pressure sensitive adhesive (PSA) applied over at least a portion of the wound facing side. The PSA is useful for initially approximating the wound. The wound closure device is preferably porous. By "porous" is meant herein either that the bulk of the wound closure device has pores, such that subsequently applied polymerizable adhesive composition is soaked up or absorbed by the bulk material, or that the bulk of the wound closure device has voids (like a net or screen), such that the subsequently applied polymerizable adhesive composition passes directly through the bulk material, with or without being soaked up or absorbed by the bulk material. For example, in the case of textile materials, "porous" is generally used to mean that the applied adhesive composition permeates and passes through interstices between the fibers, but does not necessarily pass into and through the fibers themselves. Preferably the wound closure device is a mesh strip.

Such porosity (or other properties such as hydrophobicity or hydrophilicity) will also allow a polymerization initiator or rate modifier to be loaded in or on the wound closure device prior to use, to initiate the subsequently applied polymerizable adhesive composition. Such porosity will also preferably allow air and fluid to pass through the wound closure device, either through pores per se, or through voids in the bulk material. Depending upon the degree of porosity and/or the size of the openings, such porosity of the mesh or ability of air and fluid to permeate through the mesh may be tailored either to remain after a final composite material is formed, or to be absent therefrom. The wound closure device is also preferably non-toxic, as it is intended to be used cover a wound, such as on biological tissues. As such, the wound closure device should be biologically compatible with the desired substrate (such as tissue, skin, organ, or the like), and is preferably a material that is governmentally approved or generally regarded as safe for the desired purpose. By way of example, suitable wound closure devices are mesh materials and are disclosed in United States Patent Applications 2006/0009099 and 2005/0182443, incorporated herein by reference in their entirety.

The wound closure device may be a textile or mesh/web material. Suitable textile materials may be formed of either synthetic or natural materials. Such textile material may be formed of either woven or non-woven fabrics or materials. The wound closure device may be, for example, any suitable polymeric film, plastic foam (including open celled foam), a woven fabric, knitted fabric, a non-woven fabric, mixture thereof, or the like. In particular, suitable wound closure devices may thus be prepared, for example, from nylons, polyolefins such as polyethylene, polypropylene, ethylene propylene copolymers, and ethylene butylene copolymers, acrylics, rayons, polyurethanes, polyurethane foams, polystyrenes, plasticized polyvinylchlorides, polyesters such as polyethylene terephthalate (PET), polyamides, polylactic acids, polyglycolic acids, polycaprolactones, copolymer mixtures of the above, natural materials such as cotton, silk and linen, polytetrafluoroethylene (PTFE), biovascular material, collagen, Gore-Tex®, DACRON®, etc. The preferred wound closure device materials are those that contain an OH functionality on its surface whether occurring naturally or by surface treatment to impart an OH functionality ("OH surface-treated"). These materials include and are not limited to polyesters, nylons, acrylic, rayon, polyurethanes, polyurethane foams, polystyrenes, polyesters, polyethylene terephthalate (PET), polyamides, polylactic acid, polyglycolic acid, polycaprolactone, copolymer mixtures of the above, and cotton, silk and linen. Suitable OH surface-treated materials that impart an OH functionality to their surfaces include but are not limited to OH surface-treated PTFE, OH surface-treated polypropylene and OH surface-treated polyethylene.

The wound closure device may be formed of a synthetic, semi-synthetic, or natural organic material. Thus, for example, the mesh may be formed of a synthetic or natural polymer material, but not from a material such as metal (such as silver, steel or the like) or glass or ceramic. The wound closure device may be either biodegradable, or not biodegradable. The wound closure device is preferably resistant to tearing.

The thickness of the wound closure device may be from about 0.1 mm to about 25 mm. In another embodiment, the thickness of the wound closure device is from about 0.5 mm to about 20 mm, preferably from about 0.7 mm to about 10 mm, most preferably from about 1 mm to about 5 mm.

When the wound closure device is a strip, the strip may be from about 2 cm to about 40 cm, preferably from about 10 to about 30 cm, most preferably 25 cm in length. The strip may be from 0.1 to about 8 cm, preferably from about 2 to 6 cm, more preferably about 4 cm in width.

The wound closure device may be selected to be elastic or have some memory effect. In such embodiments, the elastic properties of the mesh may desirably provide a degree of pressure or stress at the application site, for example, to maintain wound edge approximation. Likewise, in embodiments where such additional degree of pressure or stress at the application site is not desired, the mesh may be selected to have less or no elasticity.

The wound closure device may be either biodegradable, or not biodegradable. By "biodegradable" is meant that the mesh biodegrades over time in vivo, such that it does not require physical removal of the mesh after a set period of time. Thus, for example, a biodegradable mesh is one that, in the in vivo environment, will biodegrade over a period of from about one week to about five years. A nonbiodegradable material is one that does not biodegrade in an in vivo environment within about five years. Such a nonbiodegradable material thus would require physical removal of the wound closure device at a desired time, rather than slowly deteriorating over time or may slough off naturally from the tissue.

The wound closure device may include one or more chemical materials located in or on it. For example, one or more chemical substances may be dispersed in or on the wound closure device, such as being chemically bound, physically bound, absorbed, or adsorbed to it. Such chemical materials that may be present in or on the wound closure device include, but are not limited to, any suitable and preferably compatible additive that enhances performance of the composite structure. Such additional chemical substances may be bioactive or non-bioactive. Suitable other chemical substances thus include, but are not limited to, colorants (such as inks, dyes and pigments), scents, protective coatings that do not chemically detach, temperature sensitive agents, drugs, wound-healing agents, anti-microbial agents and the like.

EXAMPLES

Example 1, Novel Platinum Catalyst (Synthesis Procedure)

Figure 5:
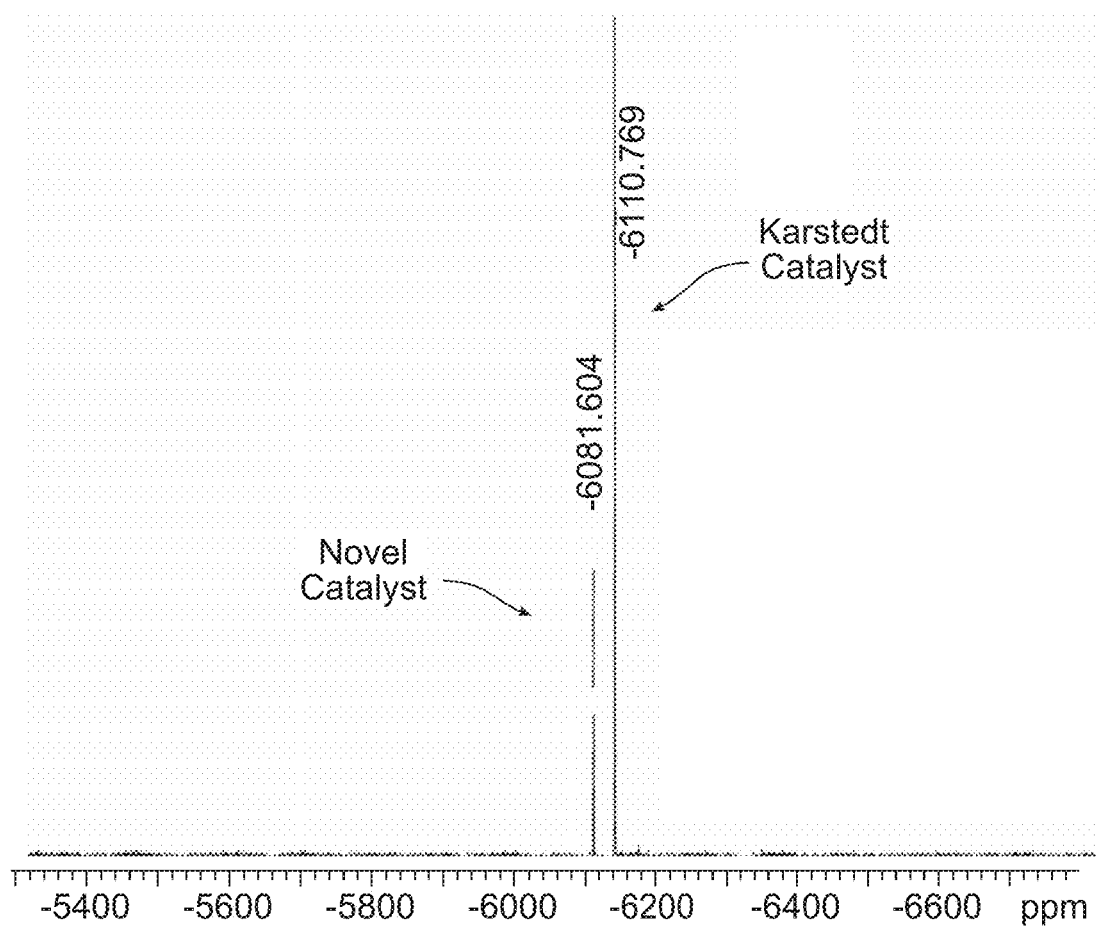
FIG. 5 is an NMR peak comparison of the Karstedt Catalyst compared with the NMR peak of the novel catalyst of this invention.

44.50 g of Gelest SIP 6831.2 (2.2% platinum divinyl tetramethyldisiloxane complex in xylene, Karstedt catalyst) was mixed with 2 g of diethyl maleate for 24 hours at ambient temperature. Samples were taken out after 3 hours, 18 hours, and 24 hours for NMR testing and the NMR spectra for the 3 hour sample is shown in FIG. 5.

The formation of the novel catalyst is the evidence for scheme 1, which rests on NMR spectroscopic identification. Karstedt catalyst is known with a characteristic $^{195}$Pt signal at approximately −6111 ppm.

After 3 hours of mixing of the mixtures of Example 1, a new $^{195}$Pt signal at −6082 ppm was observed along with the original signal for the Karstedt catalyst at −6111 ppm as illustrated in the NMR spectra of this mixture at 3 hours in FIG. 1. The intensity of the new signal increases over time while the intensity of the Karstedt catalyst signal reduced at the same time.

Example 2, Preparation of Silicone-Based Topical Skin Adhesive

In general and similar to most of commercially available platinum cured silicone materials, the silicone-based topical skin adhesive is delivered in a two-part kit by mixing equal volumes of the Part A and Part B components.

As an overview, vinyl terminated polydimethylsiloxane is mixed with platinum tetramethyldivinyl disiloxane diethyl maleate catalyst, silica particles and optionally aliphatic organic solvent using a high-speed mixer to form part A of the kit. Vinyl terminated polydimethylsiloxane were mixed with polymethylhydro-co-polydimethylsiloxane cross linker, silica particle and optionally aliphatic organic solvent using high speed mixer to form part B of the kit.

Equal amounts of the two-part kit were mixed using a static mixer and then spread onto the surface of a substrate, such as skin. The mixture of the two-part kit cured within 5 minutes at body temperature as determined by the loss of stickiness or tackiness of the applied silicone.

Part A 40 g of vinyl terminated polydimethylsiloxane (Gelest DMSV41) was mixed with 10 g of surface treated silica particles (Gelest SIS6962.0), together with 2.6 g of the resulting catalyst of Example 1 using a high-speed centrifugal mixer (FlackTek DAC150 FV-K) at 3470 rpm for 5 minutes.

Part B 40 g of vinyl terminated polydimethylsiloxane (Gelest DMSV41) was mixed with 10 g of surface treated silica particles (Gelest SIS6962.0), together with 3.34 g of Polymethylhydro-co-polydimethylsiloxane (Gelest HMS301) using a high-speed centrifugal mixer (FlackTek DAC150 FV-K) at 3470 rpm for 5 minutes.

Example 3, Preparation of Silicone-Based Topical Skin Adhesive Using Commercial Silica—Containing Silicone Raw Material Part A 90 g of Elkem 44 experimental base (containing vinyl terminated polydimethyl silicone base polymer and fume silica particles) was mixed with 4.72 g of the resulting catalyst of Example 1, 9.0 g of low molecular weight vinyl terminated polydimethyl silicone base polymer (Gelest DMS V21) and 26 g of hexane using a high-speed centrifugal mixer (FlackTek DAC150 FV-K) at 3470 rpm for 5 minutes.

Part B 81 g of Elkem 44 experimental base (containing vinyl terminated polydimethyl silicone base polymer and fume silica particles) was mixed with 8.1 g of polymethyl hydro siloxane cross linker (Gelest DMS H991), 2.7 g of SiH terminated polydimethylsiloxane chain extender (Gelest DMS H21) and 10.2 g of hexane using a high speed centrifugal mixer (FlackTek DAC150 FV-K) at 3470 rpm for 5 minutes.

Control Example: Control Example without Silica Bonding Agent and Using Conventional Karstedt Catalyst Part A 40 g of vinyl terminated polydimethylsiloxane (Gelest DMSV41) was mixed with 2.6 g of Karstedt catalyst xylene solution (1% of Gelest SIP 6831.2 in xylene) using a high-speed centrifugal mixer (FlackTek DAC150 FV-K) at 3470 rpm for 5 minutes.

Part B 40 g of vinyl terminated polydimethylsiloxane (Gelest DMSV41) was mixed 3.34 g of Polymethylhydro-co-polydimethylsiloxane (Gelest HMS301) using a high-speed centrifugal mixer (FlackTek DAC150 FV-K) at 3470 rpm for 5 minutes.

Preparation of Test Samples and Description of Test Procedures

Test Procedures

Wound Closure Strip Testing Sample Preparation:

An 8 inch by 11 inch synthetic substrate (or bio substrate) was cut in two halves with dimensions of 4 inches by 11 inches. A 1 inch wide PSA (pressure sensitive adhesive) coated polyester mesh was placed along the cutting line to hold the two half pieces together. The two-part silicone TSA compositions described above were mixed and applied onto the mesh evenly to cover the entire area of the mesh using a conventional rubber spatula.

Holding Strength Test:

This test evaluated the force required to separate the substrate approximated with the PSA coated mesh and the applied silicone TSA compositions. This method was based on ASTMF2458: Standard test method for wound closure strength in tissue adhesive and sealant.

Synthetic substrate (Mylar) were used for the test, selected samples were also tested on porcine skin. The width of the synthetic substrate was 1 inch and porcine skin was 2 inch and the strain rate was 20 inches/minute.

Peel Test.

The T-peel strength test was performed following ASTM F2256: Standard test method for Strength Properties of Tissue Adhesives in T-Peel by Tension Loading.

The average peel strength of mesh coated with silicone-based TSA in T-peel configuration is performed at a strain rate of 10 inches/minute.

Holding Strength Test Samples

Synthetic substrate, Polyester film (0.05 inch thick Duralar® film) Grafix Plastics. Maple Heights, Ohio An 8 inch by 11 inch piece of the Duralar® polyester film was cut in two half with dimensions of 4 inch by 11 inch. A 1.5 inch wide PSA (pressure sensitive adhesive) coated polyester mesh (Lot #16204, Innovize, St Paul, Minn.) was placed along the cutting line to hold the two half pieces together. The two-part silicone TSA compositions in each of the following examples were respectively mixed (Example 2, Example 3 and Control Example) and evenly applied onto the mesh to cover the entire area of the mesh using a conventional rubber spatula. The samples were dried between 2 to 5 minutes at 31 C. 5, 1 inch wide strips of each of the covered mesh samples were cut for testing.

Example 4—Silicone Film Sample

The composition of Example 3 was applied across the 2 halves of the Duralar® polyester film that were placed next to each other. The composition cured and dried to a non-tacky film to join the 2 halves together. The samples were dried between 2 to 5 minutes at 31 C. 5 pieces of 1 inch wide strips of each of the covered mesh samples were cut for testing.

Example 5—Tie Bar Samples 2 mm wide by 50 mm long pressure sensitive adhesive (PSA) coated polyester mesh were used as tie bars and placed 7 mm apart along the cutting line to hold the two half pieces of the Duralar® polyester film together and then coated with the two-part composition of Example 3. The samples were dried between 2 to 5 minutes at 31 C. 5 pieces of 1 inch wide strips of each of the covered mesh samples were cut for testing.

Example 6—Tie Bar+Mesh Strip Samples 2 mm wide by 50 mm long pressure sensitive adhesive (PSA) coated polyester mesh were placed 7 mm apart on a 1 inch by 11 inch PSA coated polyester mesh (Lot #16204, Innovize, St. Paul, Minn.). The 1 inch by 11 inch mesh was then placed along the cutting line to hold the two half pieces of the Duralar® polyester film together and then coated with the two-part composition of Example 3. The samples were dried between 2 to 5 minutes at 31 C. 5, 1 inch wide strips of each of the covered mesh samples were cut for testing.

Bio Substrate (Porcine Skin)

A 2 inch by 8 inch sample of porcine skin was cut in two halves with the dimensions of 2 inches by 4 inches. A 1.5 inch wide PSA (pressure sensitive adhesive) coated polyester mesh was placed along the cutting line to hold the two half pieces together. The two-part silicone TSA composition was mixed (Example 3) and evenly applied onto the mesh to cover the entire area of the mesh using a conventional rubber spatula.

Peel Test Samples

Synthetic substrate (Polyester film, 0.05 inch thick Duralar® film. Grafix Plastics, Maple Heights, Ohio)

A 5 inch by 5 inch PSA (pressure sensitive adhesive) coated on polyester mesh (Lot #16204, Innovize, St Paul, Minn.) was placed on the polyester substrate of the same dimensions. The two-part silicone TSA compositions of each of the following examples were respectively mixed (Example 2, Example 3, and Control Example) and applied onto the mesh evenly to cover the entire area of the mesh using a conventional rubber spatula. 5, 1 inch wide specimens were cut for testing after each of the covered mesh samples were dried.

Bio Substrate (Arm of a 55 Year-Old Asian Male)

A 3 inch by 1 inch PSA (pressure sensitive adhesive) coated on polyester mesh was placed on the left arm of a 55 year old Asian male. The two-part silicone TSA compositions of each of the following examples were respectively mixed (Example 3 and Control Example) and applied onto the mesh evenly to cover the entire area of the mesh using a conventional rubber spatula.

Bio Substrate (Porcine Skin)

A 5 inch by 1.5 inch PSA (pressure sensitive adhesive) coated on polyester mesh (Lot #16204, Innovize, St Paul, Minn.) was placed on a piece of porcine skin with approximately the same dimension. The two-part silicone TSA composition of examples 3 was mixed and applied onto the mesh evenly to cover the entire area of the mesh using a conventional rubber spatula.

Stretch Test Samples

A 5 inch by 5 inch PSA (pressure sensitive adhesive) coated polyester mesh (Lot #16204, Innovize, St Paul, Minn.) was placed on a Teflon substrate. The two-part silicone TSA composition was mixed (Example 3) and applied onto the mesh evenly to cover the entire area of the mesh using a conventional rubber spatula. The silicone coated polyester mesh was peeled off from the Teflon substrate after 1 hour. 5, 1 inch-wide silicone coated mesh specimens were cut for testing.

Additionally, a silicone only film was made from the mixed two-part silicone TSA composition of Example 3 by applying the composition to a Teflon substrate using a conventional rubber spatula and allowing the composition to cure to a non-tacky film. The film was peeled off from the Teflon substrate after 1 hour and 5, 1 inch-wide, 4 inch-long (10 cm) silicone strips were cut from the film for testing.

Performance Testing Results:

1a: Holding Test (Synthetic Substrate)

Holding test on Polyester film was performed for the compositions of Examples 2, 3, 4 and 5, along with the Control Example; the results are summarized in Table 1.

TABLE 1

| Sample | Holding Strength (lb/in) |
|---|---|
| Example 2 | 13.4 |
| Example 3 | 17.9 |
| Control Example | 0.7 |
| Example 4 | 4.0 |

TABLE 1-continued

| Sample | Holding Strength (lb/in) |
|---|---|
| Example 5 | 14.5 |
| Example 6 | 19.7 |

Referring to Table 1, it can be seen that the holding force for the polyester substrate is significantly better in the inventive examples made from polysiloxane polymer and commercial bases, compared to conventional cross-linked silicone polymer using the Karstedt catalyst (Control Example).

1b: Holding Test Results (Bio Substrate)

Holding test on porcine skin was performed on the composition of Example 3 and the results are summarized in Table 2

TABLE 2

| Sample | Holding Strength (lb) |
|---|---|
| Example 3 | 10.2 |

Referring to Table 2, one sees that the holding force of the silicone-based TSA on porcine skin is comparable to cyanoacrylate based commercial product holding strength which is about 10 lbs.

2a: Peel Test Results (Synthetic Substrate)

Peel tests of TSA compositions on a synthetic substrate (polyester) was performed using the compositions of Examples 2 and 3, along with Control Example and the results are summarized in Table 3.

TABLE 3

| Sample | Average Peel Strength (lb/in) | Maximum Peel Strength (lb/in) |
|---|---|---|
| Example 2 | 1.3 | 2.1 |
| Example 3 | 2.6 | 3.1 |
| Control Example | 0.1 | 0.2 |

Referring to Table 3, it is seen that the average and maximum peel force for polyester substrate is significantly better in the inventive examples made from polysiloxane polymer and commercial bases, compared to conventional cross-linked silicone polymers using the Karstedt catalyst.

2b: Peel Test Results (Bio Substrate)

Peel tests of TSA on human skin was performed on Example 3 and Control Example and the results are summarized in Table 4.

TABLE 4

| Sample | Average Peel Strength (lb/in) | Maximum Peel Strength (lb/in) |
|---|---|---|
| Example 3 | 2.5 | 3.5 |
| Control Example | 0.1 | 0.3 |

The peel force of silicone TSA made in inventive Example 3 is significantly higher than the Control Example. Also, the peel force of silicone TSA on human skin is very similar to the peel force of the same material on polyester substrate (see Table 3).

2b: Peel Test Results (Bio Substrate)

Peel tests of TSA on porcine skin was performed on Example 3 and the results are summarized in Table 4a.

TABLE 4a

| Sample | Average Peel Strength (lb/in) | Maximum Peel Strength (lb/in) |
|---|---|---|
| Example 3 | 0.42 | 1.04 |

3: Stretch Test Results

Figure 6A:
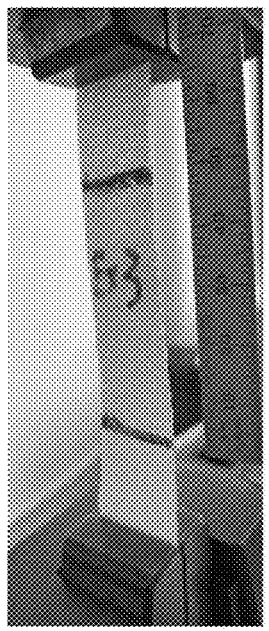
FIGS. 6a, 6b and 6c show the steps of a stretch test used to demonstrate the elasticity of a non-tie bar bearing mesh and a silicone film of the present invention.
Figure 6B:
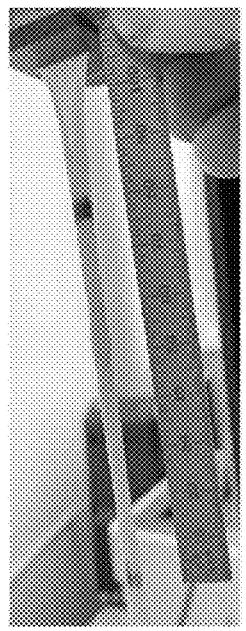
Figure 6C:
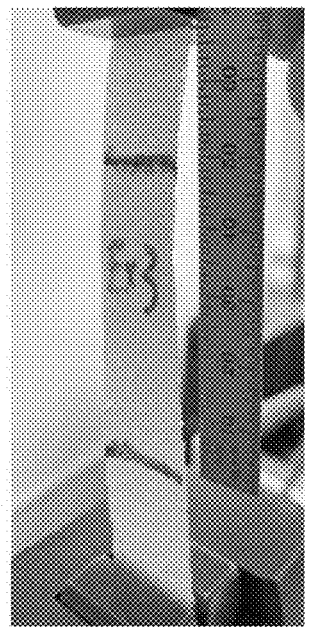

Example 3 (mesh with film) was stretched to 160% of its original length. The dimensions of the testing sample were measured before and after the stretch and the image was show in FIGS. 6a, 6b and 6c.

Figure 7A:
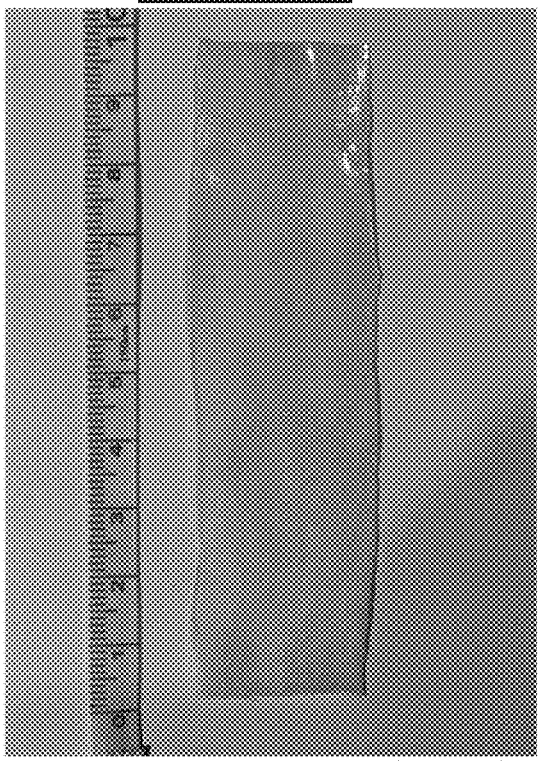
FIGS. 7a, 7b and 7c show the steps of a stretch test used to demonstrate the elasticity of a silicone film of the present invention
Figure 7B:
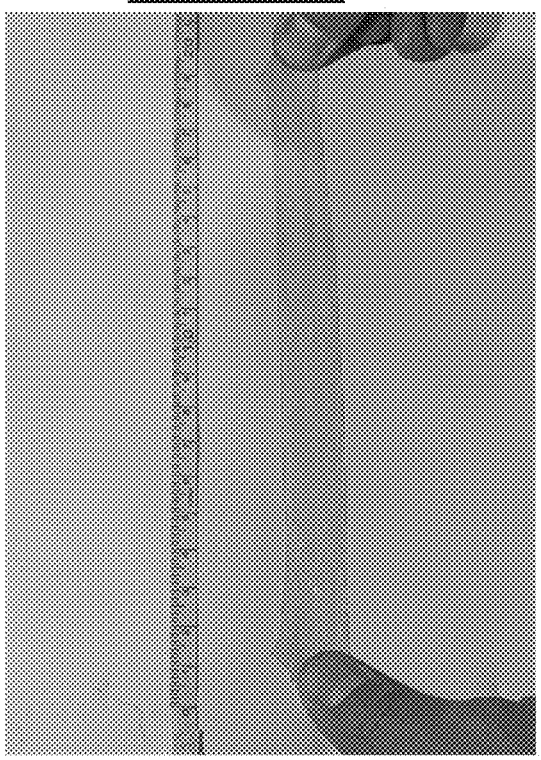
Figure 7C:
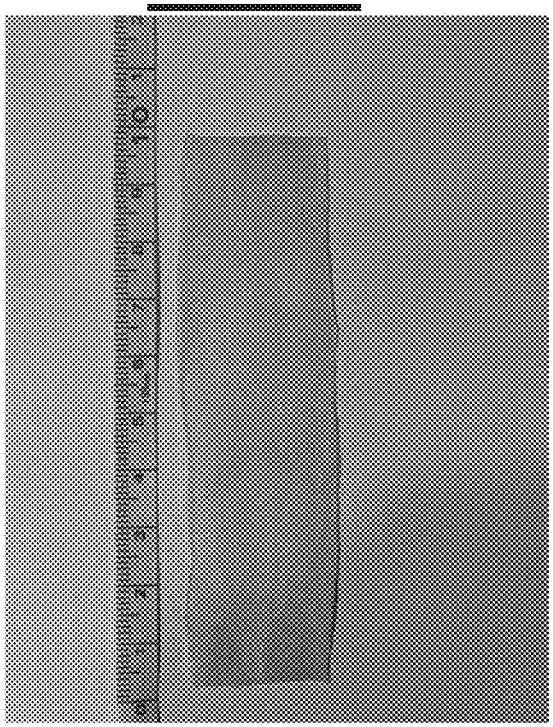

Example 4 (film alone) was manually stretched to 200% of its original length. The dimensions were measured before and after the stretch and the images are shown in FIGS. 7a, 7b, and 7c.

Figure 8A:
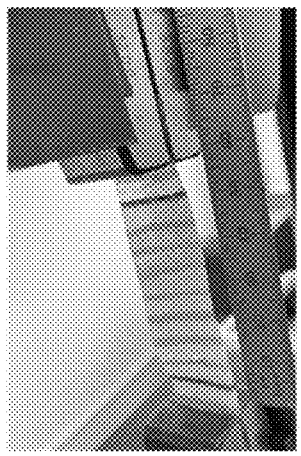
FIGS. 8a, 8b and 8c show the steps of a stretch test used to demonstrate the elasticity using tie bars and a silicone film of the present invention.
Figure 8B:
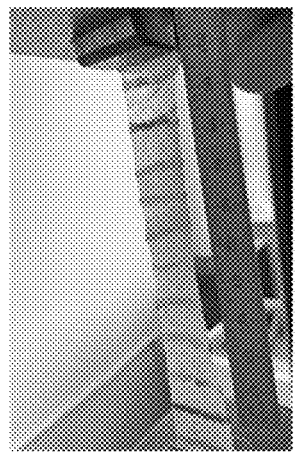
Figure 8C:
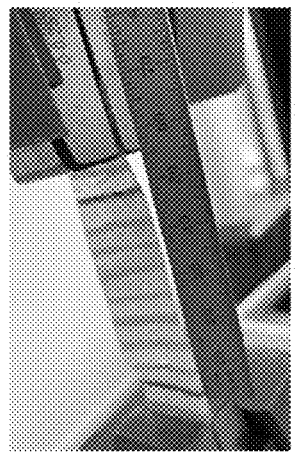

Example 5 (tie bars with film) was stretched to 160% of its original length. The dimensions of the testing sample were measured before and after the stretch and the images are shown in FIGS. 8a, 8b and 8c.

Figure 9A:
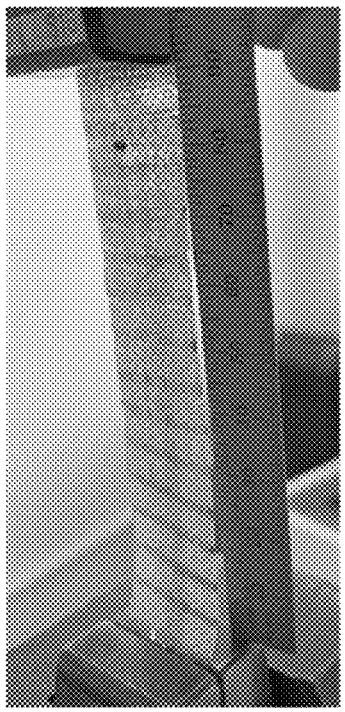
FIGS. 9a, 9b and 9c show the steps of a stretch test used to demonstrate the elasticity of a longitudinal wound closure strip with one or more tie bars incorporated across the longitudinal axis of the strip and a silicone film of the present invention
Figure 9B:
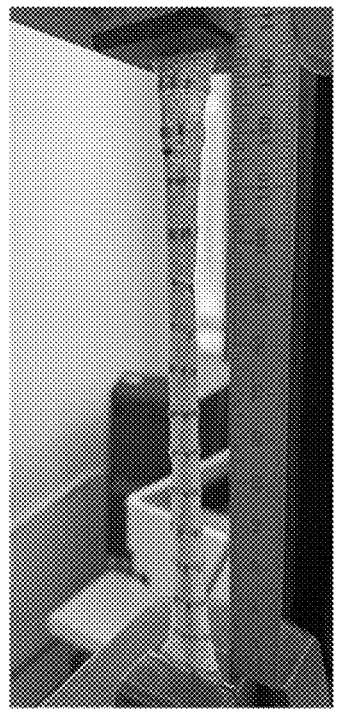
Figure 9C:
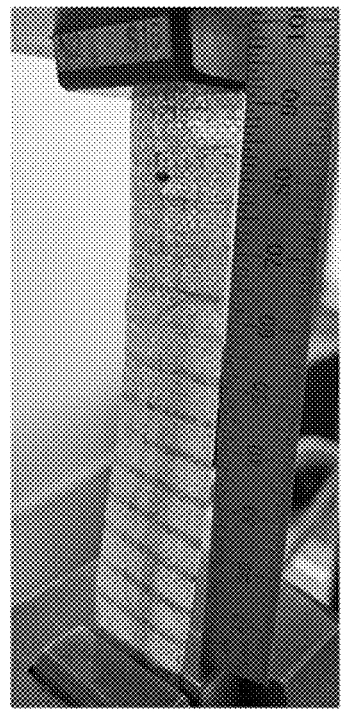

Example 6 (tie bars on mesh with film) was stretched to 150% of its original length. The dimensions of the testing sample were measured before and after the stretch and the images are shown in FIGS. 9a, 9b and 9c.

Referring to these figures, the testing results indicate that Examples 3, 4, 5 and 6 can be elongated between 150 to 200% of its original dimensions and recover fully to their original dimensions. In a separate test not depicted, a cyanoacrylate coated polyester mesh sample could only be elongated to 101% of its original dimension. That is a 1% stretch was sufficient enough to create permanent deformation.

As demonstrated, the novel compositions, wound closure systems and catalyst of the present invention have many advantages compared with the prior art. The compositions allow for the formation of medical grade silicone adhesive, in particular suitable for human skin. The compositions provide a durable elastic structure, which provides both mechanical properties and adhesion properties. The catalyst provides dual cured catalytic action, enabling the cross link of polysiloxane chains to form a film rapidly while forming adhesion properties on a given hydroxyl containing substrates. The silanol functions on the surface of silicone fillers in the compositions reacts with the hydroxyl functions on a given surface in the presence of this novel dual functional catalyst provide the adhesion properties on this novel silicone based adhesive.

Although this invention has been shown and described with respect to detailed embodiments thereof, it will be understood by those skilled in the art that various changes in form and detail thereof may be made without departing from the spirit and scope of the claimed invention.

We claim:

1. A wound closure system comprising:
   a) an anisotropic wound closure device; and
   b) a coating composition comprising:
      a cross-linkable silicone polymer having reactive functionalities;
      a silica-containing composition;
      a silicone cross-linking agent; and,
      a catalyst, wherein said catalyst comprises a platinum tetramethyldivinyl disiloxane diethyl maleate complex having the formula:

$Pt[(CH_2=CH)(CH_3)_2Si]_2O—COCH=CHCO)(C_2H_5O)_2$.

2. The system of claim 1, wherein the cross-linkable silicone polymer is selected from the group consisting of vinyl terminated polydialkylsiloxane, vinyl terminated polydimethylsiloxane, vinyl terminated polydiphenylsilane-dimethylsiloxane copolymer, vinyl terminated polyphenylmethylsiloxane, vinyl terminated polyfluoropropylmethyl-dimethylsiloxane copolymer, vinyl terminated polydiethylsiloxane, and SiH terminated polydimethyldisiloxane.

3. The system of claim 1, wherein the cross-linkable silicone polymer comprises vinyl terminated polydimethylsiloxane.

4. The system of claim 1, wherein the silica-containing composition comprises a trimethyl silyl surface treated silica filler.

5. The system of claim 1, wherein the silica-containing composition is selected from the commercially available reactive silica-containing silicone bases including HCR (high consistent rubber) bases and LSR (liquid silicone rubber) bases.

6. The composition of claim 5, wherein the silica-containing composition is a liquid silicone rubber base.

7. The system of claim 1, wherein the silicone cross-linking agent is selected from the group consisting of polymethylhydrosiloxane, polymethylhydro-co-polydimethylsiloxane, polyethyhydrosiloxane, polymethylhydrosiloxane-co-octylmethylsiloxane, and polymethylhydrosiloxane-co-methylphenylsiloxane.

8. The system of claim 1, wherein the silicone cross-linking agent comprises polymethylhydrosiloxane, polymethylhydro-co-polydimethylsiloxane and combinations thereof.

9. The system of claim 1, wherein the coating composition additionally comprises about 0 wt. % to about 30 wt. % of an organic solvent, based upon the weight of the composition.

10. The system of claim 1, wherein the coating composition comprises about 1 wt. % to about 15 wt. % of the silicone cross-linking agent based on total solids, wherein the coating composition additionally comprises about 0 wt. % to about 30 wt. % of an organic solvent, based upon the weight of the coating composition.

11. The system of claim 1, wherein the coating composition comprises about 0.003 wt. % to about 0.06 wt. % of the platinum catalyst, based on total solids, wherein the coating composition additionally comprises about 0 wt. % to about 30 wt. % of an organic solvent, based upon the weight of the coating composition.

12. The system of claim 1, wherein the coating composition additionally comprises a solvent selected from the group consisting of pentane, hexane, heptanes, mixtures of low molecular weight olefins, and combinations thereof.

13. The coating composition of claim 1, wherein the composition is curable at temperatures at about 19 C.

14. The coating composition of claim 13, wherein the composition is curable at temperatures of about 28 C in about 2-5 minutes.

15. The system of claim 1 wherein the wound closure device comprises one or more tie-bars.

16. The system of claim 1, wherein the wound closure device comprises a longitudinal wound closure strip with one or more tie bars incorporated across the longitudinal axis of the strip.

17. The system of claim 16, wherein the wound closure strip is selected from the group consisting of meshes, polymeric films, plastic foams (including open celled foam), woven fabrics, knitted fabrics, non-woven fabrics and combinations thereof.

18. The system of claim 17, wherein the wound closure strip is a mesh.

19. The system of claim 18, wherein the wound closure device comprises materials selected from the group consisting of polyesters, nylons, acrylics, rayons, polyurethanes, polyurethane foams, polystyrenes, polyesters, polyethylene terephthalate (PET), polyamides, polylactic acids, polyglycolic acids, polycaprolactones, and mixtures thereof; cotton, silk and linen; and surface-treated materials that impart an OH functionality to their surfaces including but not limited to OH surface-treated PTFE, OH surface-treated polypropylene and OH-surface treated polyethylene.

20. The system of claim 17 wherein the wound closure strip further comprises windows.

* * * * *